United States Patent [19]

Langer, Jr. et al.

[11] 4,443,545

[45] Apr. 17, 1984

[54] PROCESS FOR PRODUCING HEPARINASE

[75] Inventors: Robert S. Langer, Jr., Cambridge; Robert Linhardt, Somerville; Charles L. Cooney, Brookline; Parrish M. Galliher, West Newton, all of Mass.

[73] Assignee: Massachusetts Institute of Technology, Cambridge, Mass.

[21] Appl. No.: 337,910

[22] Filed: Jan. 8, 1982

Related U.S. Application Data

[63] Continuation-in-part of Ser. No. 180,780, Aug. 25, 1980, Pat. No. 4,341,869.

[51] Int. Cl.³ .............................................. C12N 9/88
[52] U.S. Cl. ................................................... 435/232
[58] Field of Search ........................................ 435/232

[56] References Cited

U.S. PATENT DOCUMENTS 3,549,500  12/1970  Suzuki .................................. 435/232

OTHER PUBLICATIONS

Linker et al., Methods in Enzymology, vol. 28, pp. 902–911.

Applied and Environmental Microbiology, pp. 360–365 (Feb. 1981).

Primary Examiner—Lionel M. Shapiro
Attorney, Agent, or Firm—Arthur A. Smith, Jr,; Thomas J. Engellenner

[57] ABSTRACT

Heparinase is produced by growing the bacterium, *Flavobacterium heparinum* in an improved defined medium consisting of a carbon source, two or more amino acids and several salts in the absence of protein. The carbon source concentration is specifically kept below a certain level to promote improved heparinase production. The sulfate source concentration is also specifically kept below a certain level to promote improved heparinase synthesis. Heparinase can be produced in this medium with or without the addition of an inducer compound.

5 Claims, No Drawings

PROCESS FOR PRODUCING HEPARINASE

The Government has rights in this invention pursuant to Grant Number NIH-5-RO1-GM25810-03 awarded by the Department of Health and Human Services.

REFERENCE TO RELATED APPLICATION

This application is a continuation-in-part of co-pending application Ser. No. 180,780, filed Aug. 25, 1980, now U.S. Pat. No. 4,341,869, issued July 27, 1982.

BACKGROUND OF THE INVENTION

This invention relates to an improved process for producing heparinase utilizing a defined medium with controlled concentrations of carbon source and sulfur source. Little or no heparin or other inducer is required in the medium for the synthesis of heparinase.

Heparinase is an enzyme presently used in assays for heparin. Presently heparinase is produced by *Flavobacterium heparnium* in a defined culture medium typically containing glucose, ammonium sulfate and a mixture of potassium monobasic phosphate and sodium dibasic phosphate, magnesium sulfate, trace salts, L-methionine and L-histidine and the heparinase inducer, such as sodium heparin or other salt, heparin monosulfate, hyaluronic acid, maltose, N-acetyl-D-glucosamine or the like. Certain mutants of *Flavobacterium heparinum* may not require a heparinase inducer in this medium.

Due to the high cost of potent heparinase inducers, such as heparin, it would be desirable as a first step to produce heparinase in this way by alteration of the bacterial growth medium rather than having to obtain mutants which produce heparinase without the inducer. Alternatively, it would be desirable to improve heparinase production by altering the growth medium in such a way as to improve the potency of the inducer and/or to improve the cell density levels achieved in the growth medium.

SUMMARY OF THE INVENTION

In accordance with this invention, an improved process for producing heparinase is provided wherein the chemically defined growth medium is altered to enhance the potency of the inducer, or to provide for heparinase production in the absence of the inducer. In this improved method, provision has been made to promote better heparinase production simply by achieving higher culture cell densities, with or without the addition of a heparinase inducer by controlling the concentration of the carbon source and of the sulfur source in the medium.

DESCRIPTION OF SPECIFIC EMBODIMENTS

The strain of bacterium utilized in the present invention comprises *Flavobacterium heparinum* such as *Flavobacterium heparinum* ATCC 13125 or a mutant form of this bacterium.

The bacterium utilized in the present invention is grown in a chemically defined growth medium, i.e., a growth medium devoid of proteins, yeast extract or complex nutrients which are difficult to characterize and/or which vary in characteristics depending upon their source. The carbon source which can be utilized in the growth medium can comprise glucose, glycerol, maltose or heparin at concentrations, for example, of between about 0 g/l and about 15 g/l, usually between about 10 g/l and about 12 g/l. It is preferred to utilize glucose as the carbon source at a concentration of between about 10 g/l and about 12 g/l because of low cost. It is important to maintain the concentration of the carbon source below about 15 g/l in order to enhance the potency of a heparinase inducer if present or to eliminate the need for a heparinase inducer if desired.

In addition, the growth medium contains a source of phosphate such as monobasic or dibasic potassium phosphate, sodium mono or dibasic phosphate, ammonium phosphate or mixtures thereof. The growth medium also includes a source of nitrogen such as ammonium chloride, amino acids and a source of magnesium such as magnesium chloride or magnesium phosphate. The growth medium may also include a heparinase inducer comprising sodium heparin, heparin monosulfate, hyaluronic acid, maltose, N-acetyl D-glucosamine or the like if desired. Certain mutants of *Flavobacterium heparinum* need not require a heparinase inducer.

The pH of the medium generally is maintained between about 6 and about 8, preferably about 7. It is preferred to control the pH at about 7 during the course of the fermentation by the addition of ammonium hydroxide or sodium hydroxide. Sterile air is sparged into the fermentor at a rate sufficient to meet the needs of the bacterium and typically between about 0.25 VVM and about 5.0 VVM. The dissolved oxygen is set between 0 and 100% typically at 50%. The growth medium is maintained at a temperature between about 15° C. and about 32° C., preferably between about 22° C. and about 25° C. Optionally, the growth medium can contain an antifoaming agent such as P-2000 manufactured by Dow Chemical Company at a concentration between about 0.1 ml/l and about 1 ml/l to control foaming. Also, alternatively, the growth medium can contain an amino acid or a mixture of defined amino acids such as L-histidine and L-methionine.

It is also desirable to minimize the concentration of sulfur in the growth medium in order to enhance the potency of the heparinase inducer if present or to eliminate the heparinase inducer if desired. Generally, the sulfur, other than that derived from amino acids in the growth medium, should be below about $10^{-2}$ g/l, preferably below about $10^{-4}$ g/l.

A typical altered growth medium would consist of the following defined chemicals: glucose as a carbon source, ammonium chloride as the nitrogen source, magnesium chloride, potassium mono and dibasic phosphate, L-histidine and L-methionine, trace salts comprised of $Na_2MoO_4$, $CoCl_2$, $MnCl$, $CuCl$, $FeCl$, $CaCl_2$ and antifoam. A glucose concentration would be kept below 10 g/l and above 0.1 g/l (preferably 5 g/l), and the ammonium chloride can be between 0.1 g/l and 10 g/l (preferably 2 g/l). The mixture of phosphate can comprise between about 0.1 g/l and 5 g/l (preferably 2 g/l) and the magnesium chloride between 0.1 g/l and 2 g/l (preferably 0.1 g/l). Trace salts can comprise between $10^{-5}$ M and $10^{-3}$ M (preferably $10^{-4}$ M). L-histidine and L-methionine comprise between 0.1 g/l and 1 g/l (preferably 0.5 g/l). Sulfur (besides that found in methionine) is kept as low as possible, below $10^{-4}$ g/l. Heparin or other inducers may or may not be supplied to the above medium to induce heparinase production.

A typical fermentation to produce heparinase proceeds as follows. Culture of bacteria are transferred into sterile shake flask cultures of the above medium and the flasks aerated by agitation for a certain period of time during which the bacteria grows and produces heparinase. Once grown to certain concentrations (usually 1-2 g/l dry bacterial cell weight), the culture is transferred to a preprepared presterilized fermentor containing 0.1 to 10 liters of the above medium. The medium is typically aerated at 0.1 to 1 VVM. pH is generally maintained between 6 and 8, preferably at 7 by the addition of ammonium or sodium hydroxide. Temperature is usually kept between about 15° C. and 32° C. (preferably 22°-25° C.). Cell growth continues and specific heparinase activity increases up to 7 units/mg protein (without inducer) (1 unit=1 mg of heparin degraded per hour) at a cell density of about 3-4 g/l. Further cell growth can be obtained by additions of trace amounts of sulfur source and carbon source. Culture harvest can be carried out and the heparinase further purified from the bacteria.

The following examples illustrate the present invention and are not intended to limit the same.

EXAMPLE I

Flavobacterium heparinum ATCC 13125 was grown in a 14 liter fermentor at 23° C., pH 7.0 (controlled by ammonium hydroxide addition) and aerated at a rate of 0.5 VVM with dissolved oxygen maintained at 50% of air saturation (or between 10 and 100% of air saturation). Ten liters of low sulfate culture medium was used. This medium was comprised of 10 g/l glucose, 2 g/l NH$_4$Cl, 1 g/l KH$_2$PO$_4$, 0.5 g/l MgCl$_2$, 0.1 g/l P-2000 antifoam agent (DOW), 0.5 g/l L-histidine and 0.5 g/l L-methionine, and sulfate-free trace salts at $10^{-4}$ M; sulfate was present at less than $10^{-4}$ M. Heparin or other inducers may or may not be supplied or required to produce heparinase. Heparinase may be produced in the above medium with or without the inducer to a specific activity level of 5-20 U/mg protein. After about 35 hours of growth to a cell density of 1-15 g/l dry cell weight, the cells were harvested by centrifugation at 12,840 xg, resuspended in 0.01 M phosphate buffer pH 6.8 and sonicated to release at least 90% of the cell protein. The resultant bacterial cell protein was further treated in a purification scheme to increase the purity of heparinase.

EXAMPLE II

This example is the same as the above except that further additions of glucose and sulfate source were made to obtain higher cell densities and higher heparinase titers.

After the initial growth and depletion of sulfate source and/or carbon source, either could be supplemented to the growth medium to promote further growth and further heparinase production. Typically, glucose would be added by addition of a concentrated (e.g. 200 g/l) solution to obtain a broth glucose concentration of 10 g/l. Using such an intermittent fed batch process, heparinase titers of 100,000 U/L were obtained. A sulfate source such as heparin or low concentration of inorganic sulfate would be added as a concentrate e.g. 10 g/l solution to obtain a final sulfate concentration of less than 0.01 g/l. This process can be repeated one or more times to obtain higher cell density at the time of harvest.

Such a fermentation was also run in a continuous mode by growing a batch culture to a high cell density and then beginning a continuous nutrient feed with glucose as the carbon source at low sulfate concentration (less than $10^{-4}$ M) with simultaneous continuous harvesting of the culture at the same rate. This resulted in a continuous production of cells containing heparinase with a specific activity of 8 units/mg protein.

We claim:
1. A process for producing heparinase comprising:
    (a) growing Flavobacterium heparinum in a medium, which medium comprises a carbon source having a concentration of between about 15 grams per liter and about 1 gram per liter, the medium being further defined as comprising less than about $10^{-2}$ grams per liter of sulfur, other than sulfur contained in amino acids;
    (b) harvesting at least a portion of the Flavobacterium heparinum; and
    (c) separating the heparinase from other proteins in the harvested bacteria.
2. The process of claim 1 wherein the step of growing Flavobacterium heparinum further comprises growing the bacteria in a medium substantially free of heparin and heparin salts.
3. The process of claim 1 wherein the step of growing Flavobacterium heparinum further comprises growing the bacteria in a medium substantially free of protein and yeast extracts.
4. The process of claim 1 wherein the step of separating the heparinase further comprises separating the heparinase by chromatography.
5. The process of claim 1 wherein the process is a continuous culture process.

* * * * *